(12) United States Patent
Iversen et al.

(10) Patent No.: US 6,875,747 B1
(45) Date of Patent: Apr. 5, 2005

(54) ANTISENSE TO C-MYC FOR TREATMENT OF POLYCYSTIC KIDNEY DISEASE

(75) Inventors: Patrick L. Iversen, Corvallis, OR (US); John E. Mata, Corvallis, OR (US); Vincent H. Gattone, II, Indianapolis, IN (US)

(73) Assignees: AVI Bio Pharma, Inc., Corvallis, OR (US); University of Kansas Medical Center, Kansas City, KS (US)

( * ) Notice: Subject to any disclaimer, the term of this patent is extended or adjusted under 35 U.S.C. 154(b) by 0 days.

(21) Appl. No.: 09/577,250

(22) Filed: May 24, 2000

Related U.S. Application Data (60) Provisional application No. 60/135,637, filed on May 24, 1999.

(51) Int. Cl.[7] .................... C07H 21/04; A61K 48/00; C12N 15/00
(52) U.S. Cl. .................... 514/44; 435/375; 435/377; 536/23.1; 536/24.1; 536/24.5
(58) Field of Search .................... 514/44; 435/6, 435/69.1, 91.1, 91.31, 440, 325, 352, 354, 366, 369, 375, 377; 536/23.1, 24.3, 24.31, 24.5

(56) References Cited

U.S. PATENT DOCUMENTS 6,005,094 A * 12/1999 Simon et al.

FOREIGN PATENT DOCUMENTS

WO    WO 91/09033    6/1991
WO    WO 93/23057    * 11/1993

OTHER PUBLICATIONS

Oberbauer et al., Kidney Blood Press Res 1996; 19:221–224.*
Cowley et al., Proc. Natl. Acad. Sci. USA, vol. 84, pp. 8394–8398, Dec. 1987.*
Lanoix et al., Oncogene (1996) 13, 1153–1160.*
Koul et al., Kidney International, vol. 50 (1996), pp. 1525–1530.*
Rojanasakul, Advanced Drug Delivery Reviews v. 18, 115–131 (1996).*
Summerton, J. and Weller, D., "Morpholino Antisense Oligomers: Design, Preparation, and Properties" *Antisense & Nucleic Acid Drug Development* 7:187–189 (1997).
Trudel, M., et al., "*C–MYC*–induced Apoptosis in Polycystic Kidney Disease Is Bcl–2 and p53 Independent" *J. Exp. Med.* 186(11):1873–1884 (1997).
Trudel, M., et al., "Polycystic Kidney Disease in SBM Transgenic Mice" *American Journal of Pathology* 152(1):219–229 (1998).

* cited by examiner

*Primary Examiner*—Sean McGarry
(74) *Attorney, Agent, or Firm*—Linda R. Judge; Karen Y. Hui; LeeAnn Gorthey (57) ABSTRACT

A method of treating polycystic kidney disease by administering an oligonucleotide antisense to c-myc is described. The antisense oligonucleotide is preferably a morpholino oligonucleotide.

7 Claims, 4 Drawing Sheets

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: oligonucleotide

<400> SEQUENCE: 1
acgttgaggg gcatcgtcgc                    20

<210> SEQ ID NO 2
<211> LENGTH: 20
<212> TYPE: DNA
<213> ORGANISM: Artificial Sequence
<220> FEATURE:
<223> OTHER INFORMATION: oligonucleotide

<400> SEQUENCE: 2
actgtgaggg cgatcgctgc                    20

ANTISENSE TO C-MYC FOR TREATMENT OF POLYCYSTIC KIDNEY DISEASE

This application claims priority to U.S. Provisional Application Ser. No. 60/135,637, filed May 24, 1999, expressly incorporated by reference herein.

FIELD OF THE INVENTION

The invention relates to a method and antisense conjugate for treatment of Polycystic Kidney Disease (PKD), by administration of an oligomer, antisense to c-myc.

REFERENCES

Agrawal, S. and Zhao, Q., Curr Opin Chem Biol 2:519–528, 1998.
Anderson, K. P., et al., *Antimicrob. Agents and Chemotherapy* 40(9):2004–2011, (1996)
Barisoni et al., Am J Pathol. 147(6):1728–35, 1995.
Barisoni, et al., Am J Pathol. 147(6):1728–35, 1995.
Bennett, M. R., et al., *Circulation* 92(7):1981–1993 (1995)
Calvet, J. Nephrol., 11(1):224–34, 1998.
Cowley et al., J Am Soc Nephrol 1(8):1048–53, 1991
Cowley et al., Kidney Int. 43(3):522–34, 1993.
Cowley et al., Proc Natl Acad Sci USA. 84(23):8394–8, 1987.
Dressier et al., Nature. 62(6415):65–7, 1993.
The European Polycystic Kidney Disease Consortium, 1994.
Flanagan, W. M., Cancer Metastasis Rev 17:169–176, 1998.
Gattone et al., Anat Rec. 245(3):488–99, 1996.
Gattone, V. H. et al., Lab Invest 59, 231–238, 1988.
Gattone, V. H. et al., J Lab Clin Med 12 7:214–222, 1996.
Gewirtz, A. M., Oncogene 18:3056–3062, 1999.
Grantham, JJ et al., Kidney Int 31:1145–1152, 1987.
Gregoriadis, G., Chapter 14, LIPOSOMES, DRUG CARRIERS IN BIOLOGY AND MEDICINE, pp. 287–341, Academic Press, 1979.
Hailer, H. et al., Kidney Int 53:1550–1558, 1998.
Hoang, A. T. et al., Proc Natl Acad Sci USA 91:6875–6879, 1994.
Hudziak, R. M., et al., *Antisense and Nucleic Acid Drug Dev.* 6(4):267–272 (1996)
Klingel et al., Virchows Arch B Cell Pathol Inci Mol Pathol 61(3):189–99, 1991.
Koul, H. et al. Kidney Int 50:1525–1530, 1996.
Lanoix et al., Oncogene 13(6):1153–60, 1996.
Lappalainen, et al., *Antiviral Res.* 23:119, 1994.
Lowden et al., J Lab Clin Med. 124(3):386–94, 1994.
Nass and Dickson, Clin Cancer Res. 4(7):1813–22, 1998.
Nguyen et al., Oncogene. L2(10):2109–19, 1996.
Nielsen, P. E., Annu Rev Biophys Biomol Struct 24:167–183, 1995.
Oberbauer, R. et al., Kidney Blood Press Res 19:221–224, 1996.
Pari, G. S., et al., *Antimicrob. Agents and Chemotherapy* 39(5): 1157–1161 (1995)
Rappaport, J. et al., Kidney Int 47:1462–1469, 1995.
Ryan, K. M. and Birnie, G. D., Biochem J 314:713–721, 1996.
Sakamuro, D. et al. Oncogene 11:2411–2418, 1995.
Schaffner et al., Am J Pathol. 142(4):1051–60, 1993.
Skorski, T. et al., Blood 88:1005–1012, 1996.
Stocklin et al., J Cell Biol 122(1):199–208, 1993.
Summerton, J. and Weller, D., Antisense Nucleic Acid Drug Dev 7:187–195, 1997.
Summerton, J. et al., Antisense Nucleic Acid Drug Dev 7:63–70, 1997.
Taylor, M. F. et al., Cytokine 9:672–681, 1997.
Taylor, M. F. et al., Nucleic Acid Drug Dev 8:199–205, 1998.
Thompson, E. B., Annu Rev Physiol 60, 575–600, 1998.
Torres, VE, Curr Opin Nephrol Hypertens 7(2):159–6, 1998.
Trudel et al., Mamm. Genome 5(3):149–152, 1994.
Trudel et al., J Exp Med., 186(11):1873–84, 1997
Trudel et al., Am. J. Pathol. 152(1) 219–229, 1998.
Trudel, M. et al., Kidney Int 39:665–671, 1991.
Uhlmann, et al., *Chemical Reviews*, Volume 90, No. 4, pages 544–584, June 1990.
Wages, J. M. et al., BioTechniques 23:1116–1121, 1997.
Wanke et al., Pediatr Nephrol. 5(4):513–21, 1991.
Williams, Williams, S. A., *Leukemia* 10(12):1980–1989, 1996.
Woo, D., N Engl J Med 333:1825, 1995.
Woitach et al., J Cell Biochem. 64(4):651–60, 1997.
Wu et al., Cell, 93(2): 177–88, 1998.
Wu GY and Wu CH, *J. Biol. Chem.* 262:4429–4432, 1987.
Zhan, Y. et al., Mol Cell Biol 17:6755–6764, 1997.

BACKGROUND OF THE INVENTION

Polycystic kidney disease (PKD) is a prevalent inherited disease in humans with a frequency of about 1 in 500. Adult PKD (ADPKD) is an autosomal dominant disorder affecting approximately 500,000 Americans with about 7,000 new patients identified each year. Infants with autosomal recessive (AR) PKD inherit a rapidly developing form, which can lead to renal insufficiency in the neonatal period.

The disease is characterized by the proliferation of epithelial cells, formation of renal cysts, liver cysts, intracranial aneurysm, and progression of renal insufficiency. PKD1, the gene that is mutated in approximately 85% of autosomal dominant polycystic kidney disease (ADPKD) cases in humans, has recently been identified (The European Polycystic Kidney Disease Consortium, 1994). Most mutations identified in affected families appear to be inactivating for the PKD1 and PKD2 genes. Recent evidence has suggested that a two-hit mechanism, in which the normal PKD1 allele is also inactivated, may be required for cyst growth.

The large number of genes showing abnormal expression in cystic kidneys from humans and rodents with PKD suggests that cellular processes associated with signal transduction, transcriptional regulation, and cell-cycle control are involved in cyst formation and that the cellular defect in PKD directly affects the regulation of epithelial differentiation (Calvet, 1998; Torres, 1998).

The role of c-myc in cystogenesis in the kidney and a correlation between high c-myc expression and PKD has been established. Rodent models are available to test possible therapeutic agents for efficacy against PKD (Calvet, 1998). These models take advantage of naturally occurring mutations, which confer the ARPKD and ADPKD phenotypes. The C57BL/6J-cpk/cpk mouse is a model of human ARPKD with similar renal pathology to that observed in human disease.

An approach to treating PKD based on the role of c-myc in the disease would therefore be highly desirable. To minimize complications, this approach should be efficacious in modulating the symptoms of PKD, easy to administer and without significant side effects.

BRIEF DESCRIPTION OF THE FIGURES

FIGS. 3A-A through 3E-E show the repeating subunit segment of exemplary morpholino oligonucleotides, constructed using subunits A–E, respectively, of FIG. 2.

SUMMARY OF THE INVENTION

The present invention addresses one or more of the drawbacks inherent in the prior art by providing methods for treatment of polycystic kidney disease (PKD) by administration of a morpholino-based oligomer, antisense to c-myc, where the oligomer is from 8 to 40 nucleotides in length, and has uncharged, phosphorous-containing intersubunit linkages.

Figure 3A:
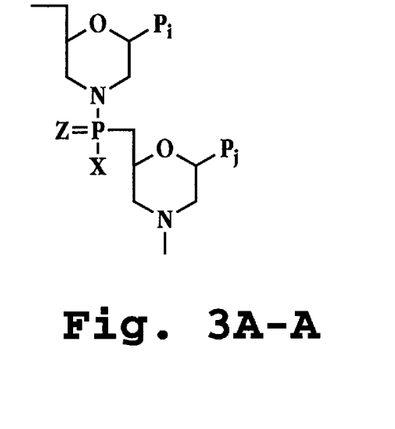
Figure 3B:
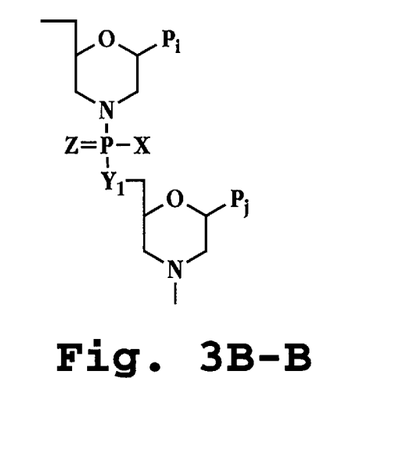
Figure 3C:
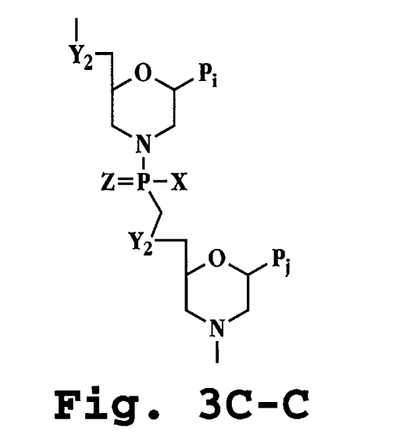
Figure 3D:
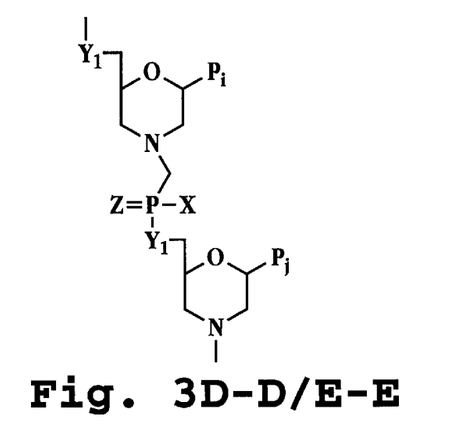

In one embodiment, the intersubunit linkages of the morpholino-based antisense oligomer are selected from the group consisting of the structures presented in FIGS. 3A-A through 3E-E, preferably including the linkage represented at FIG. 3B-B, where X=NH$_2$, Y=O, and Z=O.

In another preferred embodiment, the antisense oligomer has a length of from 12 to 25 bases, preferably having the sequence identified as SEQ ID NO:1.

In the methods of the invention, the antisense oligomer may be administered by injection, transdermal delivery, inhalation, or oral administration, and preferably the latter.

In a further preferred aspect, the subject is a human subject and the c-myc antisense oligomer is administered in a manner effective to reduce or eliminate a detectable symptom of PKD in the subject.

These and other objects and features of the invention will be more fully appreciated in conjunction with the following detailed description of the invention.

DETAILED DESCRIPTION OF THE INVENTION

I. Definitions

As used herein, the terms "antisense oligonucleotide", "antisense oligomer" and "ASO" are used interchangeably and refer to a sequence of nucleotide bases and a subunit-to-subunit backbone that allows the antisense oligomer to hybridize to a target sequence by Watson-Crick base pairing in order to form a heteroduplex with the target sequence. The oligomer may have exact sequence complementarity to the target sequence or near complementarity. Such antisense oligomers may block or inhibit translation of the mRNA containing the target sequence, or inhibit gene transcription, may bind to double-stranded or single stranded sequences, and may be said to be "directed to" a sequence with which it hybridizes.

Exemplary structures for antisense oligonucleotides for use in the invention include the β-morpholino subunit types shown in FIGS. 2A–E. It will be appreciated that a polymer may contain more than one linkage type.

Subunit A in FIG. 2 contains a 1-atom phosphorous-containing linkage which forms the five atom repeating-unit backbone shown at A—A in FIG. 3, where the morpholino rings are linked by a 1-atom phosphonamide linkage.

Subunit B in FIG. 2 is designed for 6-atom repeating-unit backbones, as shown at B—B, in FIG. 3. In structure B, the atom Y linking the 5' morpholino carbon to the phosphorous group may be sulfur, nitrogen, carbon or, preferably, oxygen. The X moiety pendant from the phosphorous may be any of the following: fluorine; an alkyl or substituted alkyl; an alkoxy or substituted alkoxy; a thioalkoxy or substituted thioalkoxy; or, an unsubstituted, monosubstituted, or disubstituted nitrogen, including cyclic structures.

Subunits C–E in FIG. 2 are designed for 7-atom unit-length backbones as shown for C—C through E—E in FIG. 3. In Structure C, the X moiety is as in Structure B and the moiety Y may be a methylene, sulfur, or preferably oxygen. In Structure D the X and Y moieties are as in Structure B. In Structure E, X is as in Structure B and Y is O, S, or NR. In all subunits depicted in FIGS. 2A–E, Z is O or S, and P$_i$ or P$_j$ is adenine, cytosine, guanine or uracil.

As used herein, a "morpholino oligomer" refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. A preferred "morpholino" oligonucleotide is composed of morpholino subunit structures of the form shown in FIG. 2B, where (i) the structures are linked together by phosphorous-containing linkages, one to three atoms long, joining the morpholino nitrogen of one subunit to the 5' exocyclic carbon of an adjacent subunit, and (ii) P$_i$ and P$_j$ are purine or pyrimidine base-pairing moieties effective to bind, by base-specific hydrogen bonding, to a base in a polynucleotide.

This preferred aspect of the invention is illustrated in FIG. 3B-B, which shows two such subunits joined by a phosphorodiamidate linkage. Morpholino oligonucleotides (including antisense oligomers) are detailed, for example, in co-owned U.S. Pat. Nos. 5,698,685, 5,217,866, 5,142,047, 5,034,506, 5,166,315, 5,185, 444, 5,521,063, and 5,506,337, all of which are expressly incorporated by reference herein.

As used herein, a "nuclease-resistant" oligomeric molecule (oligomer) is one whose backbone is not susceptible to nuclease cleavage of a phosphodiester bond. Exemplary nuclease resistant antisense oligomers are oligonucleotide analogs, such as phosphorothioate and phosphate-amine DNA (pnDNA), both of which have a charged backbone, and methyl-phosphonate, morpholino, and peptide nucleic acid (PNA) oligonucleotides, all of which have uncharged backbones.

As used herein, an oligonucleotide or antisense oligomer "specifically hybridizes" to a target polynucleotide if the oligomer hybridizes to the target under physiological conditions, with a Tm substantially greater than 37° C., preferably at least 50° C., and typically 60° C.–80° C. or higher. Such hybridization preferably corresponds to stringent hybridization conditions, selected to be about 10° C., and preferably about 5° C. lower than the thermal melting point ($T_{[m]}$) for the specific sequence at a defined ionic strength and pH. At a given ionic strength and pH, the $T_{[m]}$ is the temperature at which 50% of a target sequence hybridizes to a complementary polynucleotide.

Polynucleotides are described as "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree that one polynucleotide is complementary with another) is quantifiable in terms of the proportion of bases in opposing strands that are expected to form hydrogen bonds with each other, according to generally accepted base-pairing rules.

As used herein the term "analog" with reference to an oligomer means a substance possessing both structural and chemical properties similar to those of the reference oligomer.

As used herein, a first sequence is an "antisense sequence" with respect to a second sequence if a polynucleotide whose sequence is the first sequence specifically binds to, or specifically hybridizes with, the second polynucleotide sequence under physiological conditions.

As used herein, a "base-specific intracellular binding event involving a target RNA" refers to the specific binding of an oligomer with a target RNA sequence inside a cell. The base specificity of such binding is sequence specific. For example, a single-stranded polynucleotide can specifically bind to a single-stranded polynucleotide that is complementary in sequence.

As used herein, "nuclease-resistant heteroduplex" refers to a heteroduplex formed by the binding of an antisense oligomer to its complementary target, which is resistant to in vivo degradation by ubiquitous intracellular and extracellular nucleases.

As used herein, "c-myc", refers to an oncogene or gene that gives directs cells toward the development and growth of cancer or a tumor. "C-myc" has been associated gene amplification in various types of cancer.

As used herein, the term "c-myc antisense oligomer" refers to a nuclease-resistant antisense oligomer having high affinity (i.e., "specifically hybridizes") to a complementary or near-complementary c-myc nucleic acid sequence.

As used herein, the term "modulating expression" relative to oligonucleotides refers to the ability of an antisense oligomer to either enhance or reduce the expression of a given protein by interfering with the expression, or translation of RNA. In the case of reduced protein expression, the antisense oligomer may directly block expression of a given gene, or contribute to the accelerated breakdown of the RNA transcribed from that gene, e.g. an oncogene such as c-myc.

As used herein, "effective amount" or "pharmaceutically effective amount", relative to an antisense oligomer refers to the amount of antisense oligomer administered to a mammalian subject, either as a single dose or as part of a series of doses, that is effective to specifically hybridize to all or part of a selected target sequence, e.g. c-myc, by forming a heteroduplex between the target RNA and the antisense oligomer.

As used herein "treatment" of an individual or a cell is any type of intervention in an attempt to alter the natural course of the individual or cell. Treatment includes, but is not limited to, administration of e.g., a pharmaceutical composition, and may be prophylactic therapy, preventative therapy, or curative therapy (performed subsequent to the initiation of a pathologic event, e.g., diagnosis of PKD).

As used herein, the terms, "composition traditionally used to treat PKD" and "treating said subject, in a manner traditionally used to treat PKD" refers to treatment regimens generally used or known in the art for therapeutic intervention in a subject diagnosed as having PKD.

As used herein, "symptoms of PKD" are exemplified by abnormal levels of serum urea nitrogen (SUN), an indicator of kidney function; and/or the detection of kidney cysts, e.g., by ultrasound, computed tomography (CT) or magnetic resonance imaging (MRI).

II. Polycystic Kidney Disease (PKD)

Polycystic kidney disease (PKD) is a major cause of end stage renal disease in humans. PKD is characterized by severe dilations of collecting ducts and can be inherited as an autosomal dominant (AD) or autosomal recessive (AR) trait. In humans, ADPKD has a later onset and slower progression than ARPKD, which usually affects newborns or young children. ARPKD can cause massive bilateral enlargement of the kidneys. Most individuals surviving the neonatal period eventually develop renal failure.

The human ARPKD gene is located on chromosome 61, but has not yet been cloned. The large number of genes showing abnormal expression in cystic kidneys from humans and rodents with PKD suggests that cellular processes associated with signal transduction, transcriptional regulation, and cell-cycle control are involved in cyst formation and that the cellular defect in PKD directly affects the regulation of epithelial differentiation (Calvet, 1998; Torres, 1998). A model of cyst development has been proposed which involves an autocrine loop where cyst epithelial cells synthesize epidermal growth factor (EGF) which is secreted into cyst lumens activating EGF receptors leading to increased proliferation. The human ADPKD kidney has been shown to overexpress c-myc mRNA (Lanoix et al., 1996).

The proto-oncogene c-myc is thought to act synergistically with EGF to increase proliferation by shortening of the GI phase of the cell cycle following EGF— induced cell growth (Nass and Dickson, 1998).

It has been demonstrated that overexpression of c-myc in transgenic mice causes a greater than 4-fold increase in the expression of hepatic EGF receptors which is consistent with the hypothesis that proliferation increases with greater triggering of the EGF receptor signaling cascade (Woitach et al., 1997). This pathway for aberrant proliferation of hepatocytes may be similar in human cyst epithelium where overexpression of EGF and EGF receptors have been described for cyst-lining epithelial cells (Klingel et al., 1991).

A. Rodent Models of PKD

The C57BL/6J mouse homozygous for the congenital polycystic kidney (cpk) gene mutation is one of the most widely utilized models of ARPKD (Gattone, V. H. et al., 1988).

While the cpk gene is not analogous to the human ARPKD gene, the PKD in this well characterized mouse model exhibits bilateral renal cysts in a pattern very similar to human ARPKD. The collecting duct cysts are the predominant pathology and replace the normal renal parenchyma leading to morbid urea by four to five weeks of age.

The c-myc gene, located on mouse chromosome 15, encodes 64 to 67 kDa proteins containing domains that function in nuclear localization, non-specific and sequence-specific DNA binding, and oligomerization (Thompson, E. B., 1998). C-myc functions as a transcription factor which dimerizes with other proteins and binds DNA (Ryan, K. M. and Birnie, G. D., 1996). These heterodimeric DNA-binding complexes both activate and repress transcription of a number of genes (Hoang, A. T. et al., 1994). Increased expression of c-myc is seen in proliferating cells and regulates cell growth, transformation, inhibition of differentiation, and apoptosis (Thompson, E. B., 1998; Ryan, K. M. and Birnie, G. D., 1996).

C57BL/6J-cpk/cpk mice have previously been shown to overexpress renal c-myc mRNA (Cowley, B. D. et al., Proc. Natl. Acad. Sci. USA 84, 8394–8398, 1987; Cowley, B. D. et al., J Am Soc Nephrol, 1048–1053, 1991). The c-myc mRNA is overexpressed in epithelia from cystic as well as normal sized tubules. Renal c-myc mRNA is also overexpressed in other rodent models of PKD such as Han:SPRD-cy/cy rats, CD-1-pcy/pcy mice, and Balb-c-cpk/cpk mice. Mice that overexpress a c-myc transgene have been observed to develop PKD and die of renal failure by six weeks to three months of age (Trudel, M. et al., Kidney Int 39:665–671, 1991; Trudel, M. et al., Am J Pathol 152:219–229, 1998).

In addition, mice which have been genetically engineered to overexpress genes involved in signal transduction, cell cycle control or cellular differentiation through insertion of genes driven by active promoters often produce the PKD phenotype. For example overexpression of c-erbB-2 (Stocklin et al., 1993), c-myc (Barisoni et al., 1995), human growth hormone (hGH) (Wanke et al., 1991), human keratinocyte growth factor (hKGF) (Nguyen et al., 1996), H-rasT24 (Schaffner et al., 1993), Pax-2 (Dressier et al., 1993) and TGF-α (Lowden et al., 1994) produce renal cysts in the mouse. While PKD in the rodent appears to be genetically complicated there is reason to believe that disregulation of c-myc expression is a primary factor in the pathogenesis of PKD. ADPKD has been produced in transgenic mice bearing the murine c-myc gene driven by the SV40 enhancer and the adult beta-globin promoter producing the SBM mouse. These mice develop PKD and die of renal failure which appears to result from the overexpression of c-myc in the renal tubular epithelium leading to abnormal cell proliferation and cystogenesis (Barisoni, et al., 1995). It has been observed that in the course of continuous breeding, such transgenic lines undergo spontaneous transgene mutations characterized by partial deletion and probable rearrangement of the transgene insert, and that revertant mice and their progeny have no evidence of the disease suggesting the overexpression of c-myc is integral to the PKD phenotype in the SBM mice (Trudel et al., 1994).

Rodent models which are available to test possible therapeutic agents against PKD take advantage of naturally occurring mutations which confer the ARPKD and ADPKD phenotypes. The increase in c-myc associated with PKD was first observed in kidneys from the C57BL/6J-cpk mouse model of autosomal recessive or infantile-type PKD (Cowley et al., 1989). Recently, several investigators have backbred the cpk gene onto other mouse strains (Gattone et al., 1996).

A Balb-c model with the cpk mutation has both renal and extrarenal pathology which are similar to human ARPKD. This model allows an assessment of the effect of treatment on renal as well as extrarenal pathology. Models of slowly progressive PKD similar to human ADPKD, the more common adult onset form of the disease, include a rat model of ADPKD the Han: SPRD cy/+rat which also overexpresses c-myc (Cowley et al., 1993), which has also been used extensively to evaluate treatment approaches (Cowley et al., 1997).

B. The Role of c-myc in PKD.

Renal c-myc mRNA is overexpressed in many animal models of PKD (Trudel, M. et al., Am J Pathol 152:219–229, 1998; Gattone, V. H. et al., J Lab Clin Med 12 7:214–222, 1996). In the kidney, c-myc plays an important role in both apoptosis (Lanoix et al., Oncogene 13:1153–1160, 1996; Sakamuro, D. et al. Oncogene 11:2411–2418, 1995; Trudel, M. et al., J Exp Med 18 (6)1873–1884, 1997; Zhan, Y. et al., Mol Cell Biol 17:6755–6764, 1997), and proliferation (Lanoix et al., Oncogene 13:1153–1160, 1996; Zhan, Y. et al., Mol Cell Biol 17:6755–6764, 1997). In vitro, overexpression of c-myc promotes proliferation of cells in the presence of normal serum, but leads to apoptosis of cells in the absence of growth factors (Thompson, E. B., Annu Rev Physiol 60, 575–600, 1998). Therefore, c-myc antisense oligonucleotide (ASO) treatment has been proposed as a strategy to decrease cellular proliferation and/or apoptosis, which appear to play a role in PKD initiation and progression (Grantham, JJ et al., Kidney Int 31:1145–1152, 1987; Woo, D., N Engl J Med 333:1825, 1995).

Trudel et al., 1994, further characterized the influence of c-myc in the regulation of apoptosis through pathways involving p53 and members of the bcl-2 family, which induce and inhibit apoptosis, respectively. The SBM kidney tissues, which overexpress c-myc, displayed a markedly elevated (10–100 fold) apoptotic index while no significant difference in bcl-2, bax, or p53 expression was observed compared with control kidney tissue. Successive matings between SBM and p53(−/−) mice provided direct proof that the heightened renal cellular apoptosis in PKD is not occurring through p53. All SBM offspring, irrespective of their p53 genotype, developed PKD with increased renal epithelial apoptotic index. It was further observed that overexpression of both bcl-2 and c-myc in double transgenic mice (SBB+/SBM+) produced a similar PKD phenotype with a high apoptotic rate, showing that c-myc can bypass bcl-2 in vivo, suggesting that the in vivo c-myc apoptotic pathway in SBM mice occurs through a p53- and bcl-2-independent mechanism (Trudel et al., 1997).

Human ADPKD exhibits abnormal expression of protooncogenes with renal c-myc expression consistently elevated, as much as 15-fold. High levels of c-myc expression have been correlated with a 10- to 100-fold increased proliferation index in cystic epithelium. In addition, in the human disease, increased apoptosis has been observed in ADPKD kidneys even though steady-state levels of bcl-2 mRNA were increased up to 20-fold and Bcl-2 protein was markedly elevated with expression of bax and p53 virtually unchanged. Consistent with these observations are results from studies in SBM mice wherein proliferation and apoptosis required for normal kidney homeostasis are deregulated in ADPKD, recapitulating the renal developmental program in epithelial cells which leads to cystogenesis (Lanoix et al., 1996).

III. Methods of the Invention

The invention provides a method of treating PKD by administering to a subject, an oligomer antisense to c-myc. The invention is based on the discovery that a nuclease-resistant oligonucleotide, capable of binding with high affinity to a complementary or near-complementary c-myc sequence, can be administered to a subject, and subsequently modulate expression of c-myc in vivo in the subject, without adverse side effects. The lack of toxicity and the kidney specific modulation of epithelial proliferation following administration of an oligomer antisense to c-myc, to a subject, was not predictable based on the prior art.

Although the mechanism underlying the discovery is not part of the claimed invention, the discovery does suggest that the administered antisense oligomer is able to (i) migrate to and enter cells in the body, (ii) bind with high-affinity by Watson-Crick base pairing to complementary or near-complementary target regions of the c-myc sequence, to form a heteroduplex in the target region in the RNA, and (iii) modulate the effects of c-myc expression on epithelial proliferation, such as that observed in PKD.

A. Antisense Oligomers

Antisense oligonucleotides bind to complementary sequences, e.g., mRNA and specifically prevent nucleic acid translation, thereby disrupting gene function (Haller, H. et al., Kidney Int 53:1550–1558, 1998; Gewirtz, A. M., Oncogene 18:3056–3062, 1999). Although a number of human clinical trials are currently underway (Agrawal, S. and Zhao, Q., Curr Opin Chem Biol 2:519–528, 1998), inhibition of gene expression by ASOs has been challenging (Flanagan, W. M., Cancer Metastasis Rev 17:169–176, 1998). Inadequate specificity, ineffective delivery, instability, and unpredictable activity in cells are among the problems that have been associated with treatments involving ASO technology (Summerton, J. and Weller, D., Antisense Nucleic Acid Drug Dev 7:187–195, 1997).

C-myc ASOs have been shown to effectively inhibit c-myc induced proliferation of renal epithelial cells (Koul, H. et al. Kidney Int 50:1525–1530, 1996) as well as proliferation of chronic myelogenous leukemia cells (Skorski, T. et al., Blood 88:1005–1012, 1996) in vitro. In vivo, neointimal proliferation in injured arteries has also been demonstrated by c-myc ASO treatment (Oberbauer, R. et al., Kidney Blood Press Res 19:221–224, 1996).

Antisense technology has recently been applied to renal conditions: rats treated with ICAM-1 ASOs have exhibited reduced renal inflammation and improved renal function following anoxia reperfusion injury (Haller, H. etal., Kidney Int 53:1550–1558, 1998). It has also been demonstrated that proximal tubule cells in the kidney have the capacity to efficiently take up circulating oligonucleotides without degrading them (Rappaport, J. et al., Kidney Int 47:1462–1469, 1995).

Antisense oligonucleotides have been developed as structural DNA mimics (Nielsen, P. E., Annu Rev Biophys Biomol Struct 24:167–183, 1995), which are capable of sequence specific gene inhibition in vitro (Summerton, J. et al., Antisense Nucleic Acid Drug Dev 7:63–70, 1997; Taylor, M. F. et al., Cytokine 9:672–681, 1997; Taylor, M. F. et al., Nucleic Acid Drug Dev 8:199–205, 1998). These ASOs have a morpholino backbone giving them a neutral charge, high water solubility (Summerton, J. and Weller, D., Antisense Nucleic Acid Drug Dev 7:187–195, 1997), and resistance to nucleases (Wages, J. M. et al., BioTechniques 23:1116–1121, 1997).

Antisense oligomers for use in the methods of the invention preferably have one or more properties including: (1) a backbone which is uncharged (e.g., Uhlmann, et al., 1990), (2) the ability to hybridize with the complementary sequence of a target RNA with high affinity, that is, at a Tm substantially greater than 37° C., (3) a subunit length of at least 8 bases, generally about 8–40 bases, preferably 12–25 bases, and (4) nuclease resistance (Hudziak, et al., 1996).

Nuclease-resistant antisense oligomers which may find utility in the methods of the invention are oligonucleotide analogs, such as morpholino, methyl-phosphonate and peptide oligonucleotides, which have uncharged backbones. (See, for example, Uhlmann, et al., 1990).

Preferred antisense oligomers are nuclease-resistant oligomers with uncharged backbones, and particularly morpholino oligomers having, in addition to a base sequence complementary to a region of a selected RNA target sequence, an oligomer backbone, defined by the oligomer subunits and linkages, that allow the oligomer to bind to the target RNA sequence by Watson-Crick base pairing between complementary bases in the target RNA and the oligomer. The synthesis, structures, and binding characteristics of morpholino oligomers are detailed in above-cited U.S. Pat. Nos. 5,698,685, 5,217,866, 5,142,047, 5,034,506, 5,166,315, 5,521,063, and 5,506,337, all of which are incorporated herein by reference.

Although double-stranded DNA may be targeted by antisense molecules, in general the target for modulation of gene expression using the antisense methods of the present invention comprises a sequence spanning the mRNA translational start codon for c-myc. However, in some cases, other regions of the c-myc mRNA may be targeted, including one or more of, an initiator or promoter site, an intron or exon junction site, a 3'-untranslated region, and a 5'-untranslated region. In addition, both spliced and unspliced RNA may serve as the template for design of antisense oligomers for use in the methods of the invention.

In the methods of the invention, the antisense oligomer is designed to hybridize to a region of the c-myc nucleic acid sequence, under physiological conditions with a Tm substantially greater than 37° C., e.g., at least 50° C. and preferably 60° C.–80° C. The oligomer is designed to have high-binding affinity to the nucleic acid and may be 100% complementary to the c-myc target sequence, or may include mismatches, e.g., to accommodate allelic variants, as long as the heteroduplex formed between the oligomer and c-myc target sequence is sufficiently stable to withstand the action of cellular nucleases and other modes of degradation during its transit from cell to body fluid. Mismatches, if present, are less destabilizing toward the end regions of the hybrid duplex than in the middle. The number of mismatches allowed will depend on the length of the oligomer, the percentage of G:C base pair in the duplex and the position of the mismatch(es) in the duplex, according to well understood principles of duplex stability.

Antisense oligonucleotides of 15–20 bases are usually long enough to have one complementary sequence in the mammalian genome. In addition, antisense compounds having a length of at least 17 nucleotides in length hybridize well with their target mRNA (Cohen, et al., 1991).

It will be appreciated that although such an antisense oligomer is not necessarily 100% complementary to the c-myc target sequence, it is effective to stably and specifically bind to the target sequence such that expression of c-myc is modulated. The appropriate length of the oligomer to allow stable, effective binding combined with good specificity is about 8–40 nucleotide base units, and preferably about 12–25 nucleotides. Oligomer bases that allow degenerate base pairing with target bases are also contemplated, assuming base-pair specificity with the target is maintained.

Candidate antisense oligomers are evaluated, according to well known methods, for acute and chronic cellular toxicity, such as the effect on protein and DNA synthesis as measured via incorporation of $^3$H-leucine and $^3$H-thymidine, respectively. In addition, various control oligonucleotides, e.g., control oligonucleotides such as sense, nonsense or scrambled antisense sequences, or sequences containing mismatched bases may be evaluated, in order to confirm the specificity of binding of candidate antisense oligomers. The outcome of such tests are important to discern specific effects of antisense inhibition of gene expression from indiscriminate suppression. (See, e.g. Bennett, et al., 1995). Accordingly, sequences may be modified as needed to limit non-specific binding of antisense oligomers to non-target sequences.

It is generally desirable that non-specific binding of the oligomeric molecule t6 non-target sequences be limited. Although some non-sequence-specific interactions of such oligomers may show therapeutic effects (e.g. Anderson, K. P., et al., 1996), such interactions often produce unwanted side effects. To test for non-specific binding, control sequences such as sense or nonsense sequences, or sequences containing mismatched bases, may be included in preliminary screening tests (in vitro). Excess targeted protein or mRNA may also be added to the cell culture to see if the effect of the antisense oligomer is reversed (Bennett, M. R., et al., 1995).

Additional sequences may be prepared by one of skill in the art, having in mind one or more desired target sequences, with screening carried out according to methods routinely employed by those of skill in the art.

The effectiveness of a given oligomer molecule in forming a heteroduplex with the target RNA may be determined by screening methods known in the art. For example, the oligomer is incubated in vitro with cells that express c-myc, and the presence or absence of a heteroduplex detected using procedures known to those of skill in the art, or the presence or absence of the encoded protein determined by standard techniques such as ELISA or Western blotting (see, for example, Pari, G. S. et al., 1995; Anderson, K. P., et al., 1996). It is generally desirable that non-specific binding of the oligomeric molecule to non-target sequences is limited.

As noted above, the antisense oligomer should have a high affinity for its target sequence. In this regard, morpholino oligomers, such as illustrated below, afford exceptional target binding affinity, especially for RNA targets. They are also highly resistant to degradation by nucleases (Hudziak, R. M., et al., 1996). These compounds are composed of morpholino subunit structures of the form shown in FIGS. 2A–E and 3AA–EE and in the above cited patents, where (i) the morpholino groups are linked together by preferably uncharged linkages, one to three atoms long, joining the morpholino nitrogen of one subunit to the 5' exocyclic carbon of an adjacent subunit, and (ii) the base attached to the morpholino group is a purine or pyrimidine base-pairing moiety effective to bind, by base-specific hydrogen bonding, to a base in a polynucleotide. The purine or pyrimidine base-pairing moiety is typically adenine, cytosine, guanine, uracil or thymine. Preparation of such oligomers is described in detail in U.S. Pat. No. 5,185,444 (Summerton and Weller, 1993), which is hereby incorporated by reference in its entirety. As shown in this reference, several types of nonionic linkages may be used to construct a morpholino backbone.

Although targeting of a messenger RNA sequence is preferred, double-stranded DNA may be targeted by using a non-ionic probe designed for sequence-specific binding to major-groove sites in duplex DNA. Such probe types are described in U.S. Pat. No. 5,166,315 (Summerton and Weller, 1992), which is hereby incorporated by reference, and are also generally referred to herein as antisense oligomers, referring to their ability to block expression of target genes.

Morpholino oligomers can be linked in a polymeric form by stable, uncharged backbone linkages, and can hybridize with a complementary-base target nucleic acid, including target RNA, with high affinity. This combination of properties, which is related to subunit coupling through each morpholino subunit's ring nitrogen, is not found in natural polynucleotides or in polynucleotides containing various charged or uncharged linkages or in polynucleotides containing "one or more" analogs of naturally occurring nucleotides.

A preferred antisense oligomer for use in the methods of the invention has the sequence presented as 5'-ACG TTG AGG GGC ATC GTC GC-3' (oligonucleotide 1–22-126; SEQ ID NO:1).

B. In vivo Administration of Antisense Oligomers.

Effective delivery of the antisense oligomer to the target RNA is an important aspect of the methods of the invention. In accordance with the invention, such routes of antisense oligomer delivery include, but are not limited to, various systemic routes, including oral and parenteral routes, e.g., intravenous, subcutaneous, intraperitoneal, and intramuscular, as well as inhalation and transdermal delivery.

It is appreciated that any methods which are effective to deliver the c-myc antisense oligomer to the target cells or to introduce the drug into the bloodstream are also contemplated.

Transdermal delivery of antisense oligomers may be accomplished by use of a pharmaceutically acceptable carrier adapted for e.g., topical administration. One example of morpholino oligomer delivery is described in PCT patent application WO 97/40854, incorporated herein by reference.

In one preferred embodiment, the oligomer is a morpholino oligomer, contained in a pharmaceutically acceptable carrier, and delivered orally. In a further aspect of this embodiment, a morpholino c-myc antisense oligonucleotide is administered at regular intervals for a short time period, e.g., daily for two weeks or less. However, in some cases the antisense oligomer is administered intermittently over a longer period of time.

Typically, one or more doses of antisense oligomer are administered, generally at regular intervals for a period of about one to two weeks. Preferred doses for oral administration are from about 1 mg oligomer/patient to about 25 mg oligomer/patient (based on an adult weight of 70 kg). In some cases, doses of greater than 25 mg oligomer/patient may be necessary. For IV administration, the preferred doses are from about 0.5 mg oligomer/patient to about 10 mg oligomer/patient (based on an adult weight of 70 kg).

The antisense compound is generally administered in an amount sufficient to result in a peak blood concentration of at least 200–400 nM c-myc antisense oligomer.

In general, the method comprises administering to a subject, in a suitable pharmaceutical carrier, an amount of an antisense agent effective to inhibit expression of the c-myc nucleic acid sequence in vivo in the kidney.

It follows that the antisense oligonucleotide composition may be administered in any convenient vehicle, which is physiologically acceptable. Such an oligonucleotide composition may include any of a variety of standard physiologically acceptable carrier employed by those of ordinary skill in the art. Examples of such pharmaceutical carriers include, but are not limited to, saline, phosphate buffered saline (PBS), water, aqueous ethanol, emulsions such as oil/water emulsions, triglyceride emulsions, wetting agents, tablets and capsules. It will be understood that the choice of suitable physiologically acceptable carrier will vary dependent upon the chosen mode of administration.

In some instances liposomes may be employed to facilitate uptake of the antisense oligonucleotide into cells. (See, e.g., Williams, 1996; Lappalainen, et al., 1994; Uhlmann, et al., 1990; Gregoriadis, 1979.) Hydrogels may also be used as vehicles for antisense oligomer administration, for example, as described in WO 93/01286. Alternatively, the oligonucleotides may be administered in microspheres or microparticles. (See, e.g., Wu and Wu, 1987).

Sustained release compositions are also contemplated within the scope of this application. These may include semipermeable polymeric matrices in the form of shaped articles such as films or microcapsules.

In preferred applications of the method, the subject is a human subject, previously diagnosed as having PKD or at risk for developing PKD.

It will be understood that the effective in vivo dose of the c-myc antisense oligonucleotides for use in the methods of the invention will vary according to the frequency and route of administration as well as the condition of the subject under treatment. Accordingly, such in vivo therapy will generally require monitoring by tests appropriate to the condition being treated and a corresponding adjustment in the dose or treatment regimen in order to achieve an optimal therapeutic outcome.

It will further be appreciated that the use of a c-myc antisense oligonucleotide to treat PKD may be used following, concurrently with and/or prior to additional therapeutic intervention, e.g., using a therapeutic approach typically used by those of skill in the art to treat PKD.

C. Monitoring Treatment.

The efficacy of a given therapeutic regimen involving the methods described herein, may be monitored by one or more of (1) histology or immunohistology, by staining kidney cells or tissue sections to evaluate the status of the kidney, e.g., with monoclonal or polyclonal antibodies to c-myc; (2) analysis of RNA to quantitate the transcription of c-myc or another mRNA, e.g., by dot blot, Northern blot or RT-PCR (reverse transcriptase polymerase chain reaction); (3) in situ hybridization, e.g., using c-myc as a probe; (4) western blot analysis; (5) a determination of total body weight, total kidney weight and kidney weight as a percent of body weight; (6) a determination of serum urea nitrogen (SU4), as an indicator of kidney function; (7) hematocrit; and (8) detection of cysts, e.g., by ultrasound, computed tomography (CT) or magnetic resonance imaging (MRI). Numerous example of such methods are generally known in the art, some of which are further described below.

The antisense oligomer treatment regimen may be adjusted (dose, frequency, route, etc.), as indicated, based on the results of the various assays described above.

Additional information relevant to treatment with c-myc antisense oligonucleotides may be obtained by one or more of: (1) extraction and analysis of c-myc ASO levels in various tissues; (2) a determination of epidermal growth factor (EGF) expression, typically highly expressed in normal kidney, the expression of which is significantly diminished in cystic kidney; (3) evaluation of the expression of SGP-2, a marker of immature collecting ducts, typically overexpressed in cystic versus normal kidney; and (4) evaluation of the expression of renal proliferating cell nuclear antigen (PCNA), a marker of cell proliferation.

The following example illustrates but is not intended in any way to limit the invention.

Materials And Methods

Immunohistology.

Paraffin sections of kidneys from c-myc ASO treated and untreated normal and cystic mice may be analyzed by immunohistochemistry for c-myc. Typically, 20 day old mice are used for such analyses. One exemplary method includes the following steps: kidney sections are prepared, then endogenous peroxidase activity is quenched with methanolic peroxide, and tissue sections are treated with normal goat blocking serum. Kidney sections are then incubated with a rabbit polyclonal antibody to human c-myc (catalog # sc-764, a Santa Cruz Biotechnology, Inc., Santa Cruz, Calif.) at a dilution of 1:25 for 18 hours at 4° C. The bound antibody is visualized using an avidin biotin complex method (Vector Laboratories, Burlingame, Calif.) with nickel enhanced DAB as the chromagen. Negative control sections are processed in an identical manner, using normal rabbit serum in place of the primary antibody.

RNA Isolation and Northern Hybridization.

RNA may be extracted and purified from kidneys of normal and cystic mice as well as c-myc ASO and scrambled oligonucleotide treated normal and cystic mice using any of a number of methods known in the art. Typically 20 day old mice are used for such analyses.

In one approach, the acid guanidinium thiocyanate-phenol-chloroform extraction method is used. Briefly, frozen kidneys are homogenized in Tri-Reagent (Molecular Research Center, Inc., Cincinnati, Ohio) and RNA is isolated according to the manufacturer's instructions. The RNA is separated on a 1% agarose/formaldehyde gel via electrophoresis, with each lane containing ten $\mu$g of total renal RNA. The RNA is then transferred overnight to a Zetabind membrane (Cuno, Inc., Meriden, Conn.), and stained with methylene blue to ensure equivalent amounts of RNA in each lane. The membrane is then baked (2 hours at 80 degrees C.) and hybridized overnight at 65° C. in Church's buffer (1% BSA and 7% SDS in 0.5M sodium phosphate with 1 mM EDTA) with $^{32}$P-labeled cDNA probes (random prime labeling method, Rediprime II, Amersham Pharmacia Biotech, Arlington Heights, Ill.). Hybridized Northern blots are washed for ten minutes each at 65° C.; twice in Wash Buffer A (0.5% BSA and 5% SDS in 40 mM sodium phosphate and 1 mM EDTA), and four times in Wash Buffer B (1% SDS in 40 mM sodium phosphate and 1 mM EDTA). Autoradiography is used to visualize the relative expression of mRNA. Specific mRNA may be quantitated using densitometry of the autoradiograph. Northern blot hybridization studies are generally performed in duplicate with different sets of RNAs.

Western Blot Analysis

Protein from kidneys of normal and cystic mice as well as c-myc ASO and scrambled oligonucleotide treated normal and cystic mice may also be analyzed using any of a number of methods known in the art.

In one exemplary approach, fresh kidneys from c-myc ASO treated and untreated C57BL/6J-cpk/cpk mice are removed at 21 days and immediately homogenized in Radio Immuno Precipitation Assay (RIPA) buffer (1×PBS, 1% Nonidet P-40, 0.5% deoxycholic acid, 0.2% SDS) containing protease inhibitors (catalog # 1836170, Boehringer Mannheim, Mannheim, Germany). Protein is isolated and processed for western blot analysis by standard techniques. Protein samples are then separated on a 12.5% SDS/acrylamide gel with a 6% SDS/acrylamide stacking gel at 33 mA for 14 h. The gels are soaked in transfer buffer (192 mM glycine, 25 mM Tris base, and 10% methanol, pH 8.3) for 20 minutes and transferred to Immobilon-P transfer membranes (Millipore Corporation, Bedford, Mass., at 80 volts for 80 minutes). The membranes are soaked briefly in methanol and dried at 40° C., then rehydrated briefly in methanol, rinsed in wash buffer (PBS with 0.3% Tween 20) and incubated in blocking buffer (PBS, 0.3% Tween 20 and 3% powdered milk) for 30 minutes. Membranes are then incubated for one hour with primary antibodies to: c-myc (catalog # sc-764, Santa Cruz Biotechnology, Inc., Santa Cruz, Calif.), glucocorticoid receptor (catalog # sc-1004, Santa Cruz Biotechnology, Inc., Santa Cruz, Calif.), or proliferating cell nuclear antigen (PCNA; catalog # sc7907, Santa Cruz Biotechnology, Inc., Santa Cruz, Calif.) each at a 1:500 dilution in blocking buffer. The membranes are washed 3 times for 5 minutes with wash buffer and incubated for 30 minutes with the appropriate horse radish peroxidase (HRP) conjugated secondary antibody. Membranes are rinsed again with wash buffer and incubated with ECL detection reagent (Promega Corp., Madison, Wis.) followed by autoradiography using Kodak Bio Max film.

Extraction and Analysis of Renal c-myc ASO.

The amount of antisense oligonucleotide in the target tissue may also be analyzed. In one exemplary method of analysis, 500 ng of an internal standard oligonucleotide or a 15mer phosphorodiamidate morpholino oligomer whose sequence was derived from a 5' truncation of the c-myc ASO is mixed with a 500 $\mu$l aliquot of kidney lysate prepared in RIPA buffer. An equal volume of methanol is added, and the resulting precipitate centrifuged for 10 minutes. The supernatant is collected, the pellet washed with 100 $\mu$l of 0.025M Tris buffer (pH 9.0) and recentrifuged. The resulting supernatants are collected, heated at 70° C. for 10 minutes and recentrifuged. The supernatant is lyophilized following the addition of 100 $\mu$l of 0.025M Tris buffer (pH 9.0). The resulting viscous oily residue is reconstituted with 100 $\mu$l of a 5'-fluorescein labeled DNA (FDNA, Hybridon, Inc., MA) solution (0.2 OD 's in 100 $\mu$l of 0.025M Tris buffer). The FDNA has a complementary sequence to that of the c-myc ASO and forms a stable duplex. The entire sample is injected and analyzed by HPLC (Varian 9010 HPLC pump, Palo Alto, Calif., attached to a Rainin A1-200 autosampler and a Varian 9075 Fluorescence detector connected to a DNAPac PA-100 anion exchange column, Dionex Corp., Sunnyvale, Calif.).

A binary gradient (10% B at 0 minutes to 45% B at 20 minutes) consisting of 0.025M Tris buffer (pH 9.0) as mobile phase A and 0.025M Tris buffer (pH 9.0)/1M NaCl as mobile phase B is used to achieve the chromatographic separation. The fluorescence excitation and emission wavelengths are set at 494 nm and 518 nm, respectively. The amount of the c-myc ASO present in the kidney lysate samples may then be determined using a standard curve generated by running a series of c-myc ASO standards containing the internal standard.

Statistical Analysis. Statistical analysis of serum urea nitrogen, total body weight, kidney weight as a percent of body weight, and hematocrit are performed using analysis of variance (ANOVA) ($p<0.05$) with the aid of MINITAB software (State College, Pa.). Data are presented as mean±SEM.

EXAMPLE 1

In order to evaluate the association of c-myc mRNA expression to PKD, C57BL/6J-cpk/cpk mice were treated with a c-myc antisense oligonucleotide. C57BL16J-cpk/cpk mice (KU Medical Center from stock originally obtained from Jackson Laboratory, Bar Harbor, Me.) were bred to produce control/normal (+/+ or cpk/+) and cystic (cpk/cpk) mice. cpk/cpk and control mice were treated with a morpholino oligonucleotide antisense to c-myc at a dose of 4.3 nmoles (30 µg/mouse/day), injected intraperitoneally (IP) on postnatal days 7 through 20.

Some mice were treated with higher (14.3 nM; 100 µg) or lower (1.4 nM; 10 µg) dosages of the c-myc antisense oligomer (ASO). The c-myc ASO had a morpholino backbone with a nucleotide sequence presented as 5'-ACG TTG AGG GGC ATC GTC GC-3' (oligonucleotide 1-22-126; SEQ ID NO:1). As controls, mice were either sham injected or given an equal amount of a scramble ASO with a nucleotide sequence presented as 5'-ACT GTG AGG GCG ATC GCT GC-3' (oligonucleotide 1-22-144; SEQ ID NO:2). These mice were sacrificed four hours after the last injection. Control, scrambled and c-myc ASO treated C57BL/6J-cpk mice were anesthetized (65 mg/kg sodium pentobarbital, IP) and sacrificed at 20 days of age.

Total body weight, total kidney weight and kidney weight as a percent of body weight were determined. Blood was collected from the heart, the hematocrit measured and the serum used to assess renal function. Serum urea nitrogen (SUN) was determined utilizing a colorimetric assay (Sigma #640, Sigma Chemical Co., St. Louis, Mo.). Table I and FIGS. 1A–D illustrates the results of these analyses reported as kidney weight as a percentage (%) of body weight (BW); serum urea nitrogen (SUN) (mg/dl); total body weight (g); and hematocrit.

TABLE 1

Comparison Of Antisense c-myc Treated And Untreated Cystic And Normal Mice.

|  |  | c-myc AS Oligo [1](5/15) | Scrambled Oligo (8/12) | Sham (6/6) |
|---|---|---|---|---|
| Kidney Weight as % BW | cystic[2]** | 11.90 ± 0.045* | 17.93 ± 0.65 | 19.13 ± 1.89 |
|  | normal | 1.64 ± 0.02 | 1.54 ± 0.021 | 1.42 ± 0.05 |
| SUN (mg/dl) | cystic** | 38.4 ± 3.20* | 59.8 ± 4.83 | 61.9 ± 10.2 |
|  | normal | 17.5 ± 0.66 | 20.4 ± 0.74 | 18.8 ± 1.43 |
| Total Body Weight (g) | cystic | 9.02 ± 0.40 | 9.98 ± 0.30 | 9.34 ± 0.53 |
|  | normal | 10.08 ± 0.42 | 9.53 ± 0.34 | 9.51 ± 0.37 |
| Hematocrit | cystic** | 22.0 ± 1.6 | 25.6 ± 0.98 | 24.2 ± 4.3 |
|  | normal | 31.7 ± 0.45 | 30.5 ± 1.01 | 33.2 ± 2.01 |

Figure 1A:
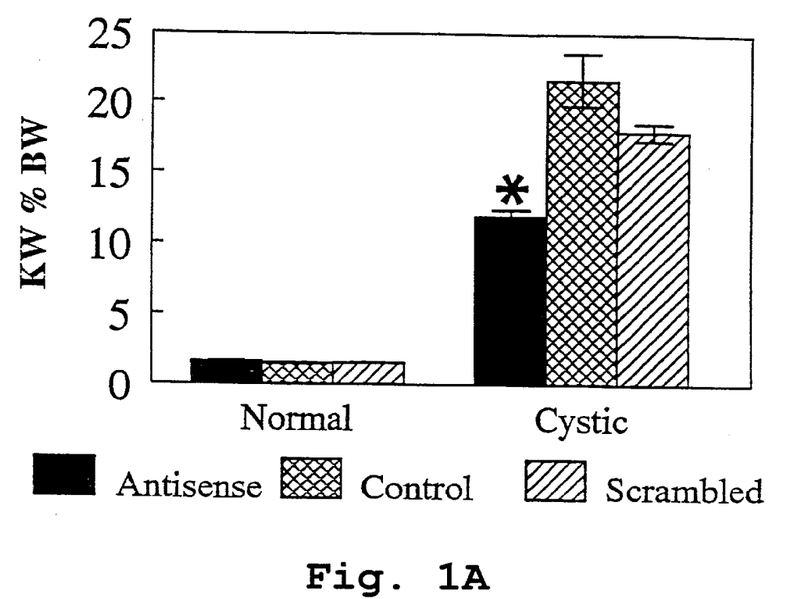
FIGS. 1A–D illustrate the effects of c-myc antisense oligonucleotide treatment in 20 day old normal and cystic C57BL/6J mice on (A) kidney weight as a percentage of body weight (relative kidney weight); (B) serum urea nitrogen (SUN); (C) total body weight; and (D) hematocrit.
Figure 1B:
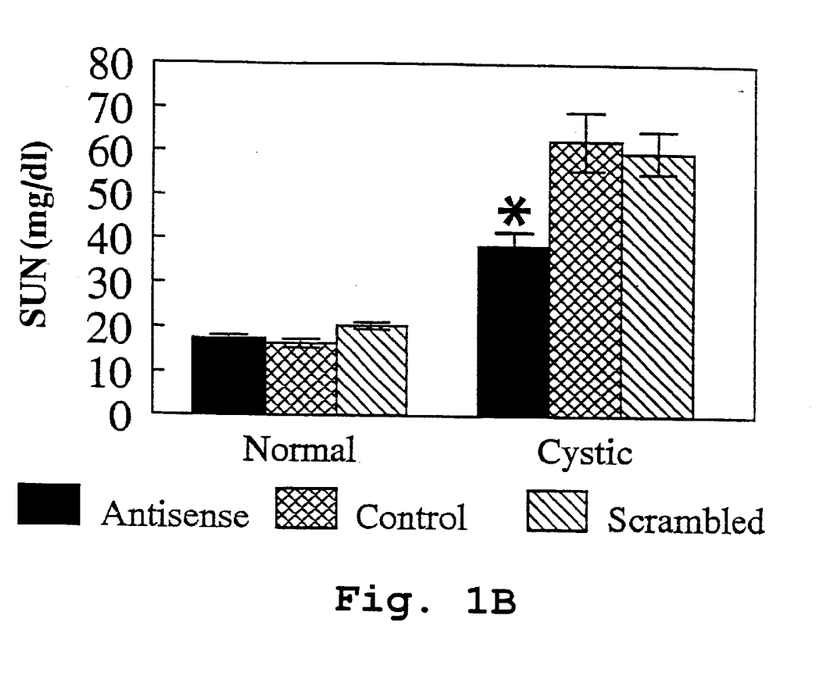
Figure 1C:
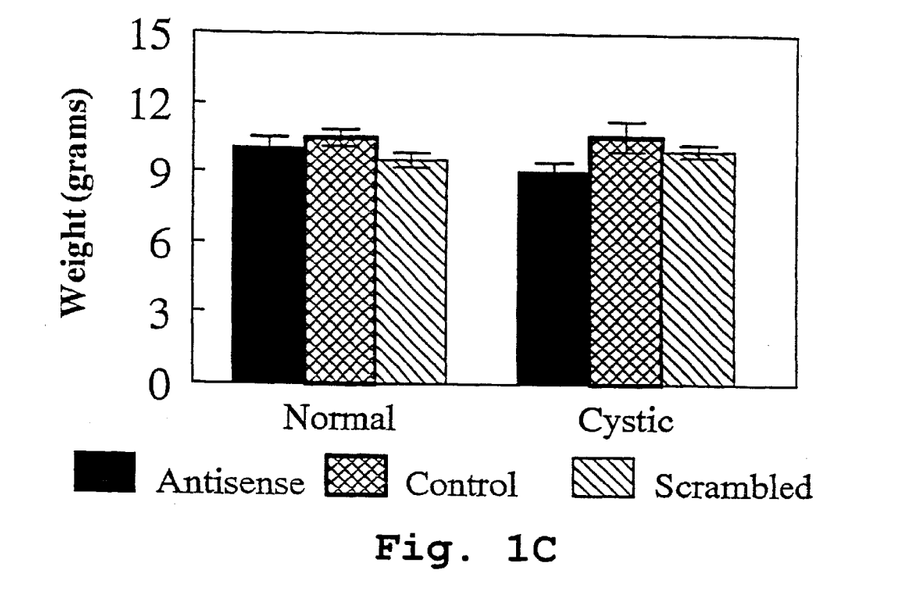
Figure 1D:
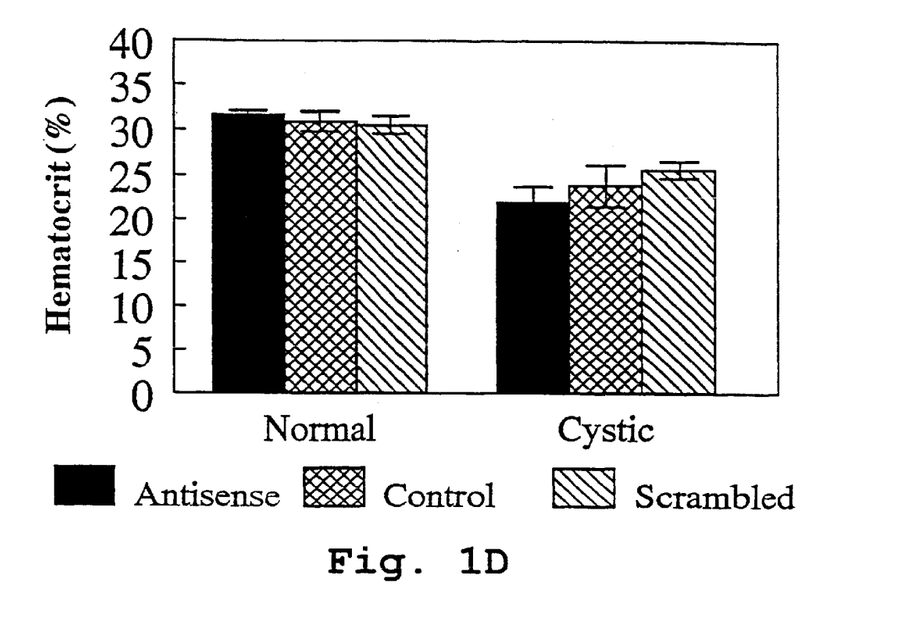
Figure 2A:
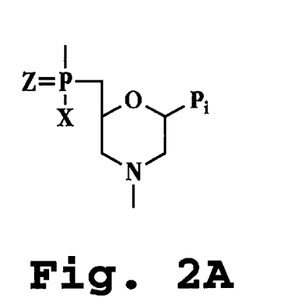
FIGS. 2A–E shows several preferred morpholino subunits having 5-atom (A), six-atom (B) and seven-atom (C–E) linking groups suitable for forming polymers.
Figure 2B:
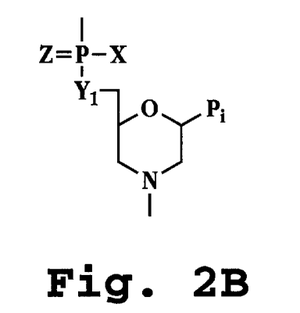
Figure 2C:
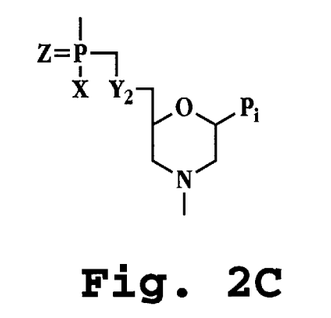
Figure 2D:
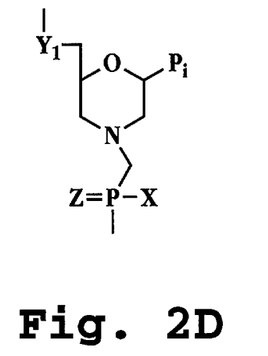
Figure 2E:
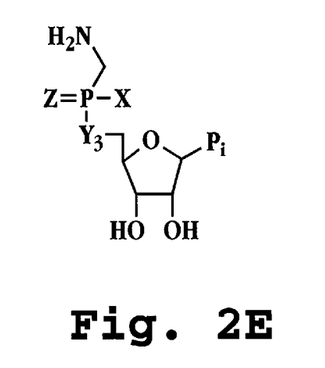

[1]*$p < 0.05$ for difference with AS treatment
[2]**$p = 0.05$ for difference from normal c-myc AS treatment significantly reduced the degree of renal enlargement as shown in FIG. 1A (11.91±0.45% versus 21.68±1.88% in control mice, $p<0.05$) and inhibited the decline in renal function as shown in FIG. 1B, (38.42±3.20 mg/dl versus 62.4±6.80 mg/dl in control cystic mice, $p<0.05$). Renal function was improved in treated cystic mice as evidenced by a decreased SUN. The c-myc antisense treatment had no effect on total body weight or hematocrit indicating no detrimental effect on highly proliferative processes such as growth and hematopoiesis (FIGS. 1C and D, respectively).

In order to further analyze the mice, the left kidney was removed, weighed, snap frozen in liquid nitrogen, and stored at −80° C. until processed for RNA isolation. The animals were then perfusion fixed with 4% paraformaldehyde in 0.1M phosphate buffer through the left ventricle. The right kidney was processed for paraffin embeddment and sections were stained with periodic acid Schiffs reaction or immunostained for c-myc.

Microscopic analysis of kidney sections indicated that while ASO treatment slowed renal enlargement, the ASO treated C57BL6J-cpk/cpk kidneys still exhibited significant cystic pathology, while no renal changes were seen in normal C57BL/6J mice following c-myc ASO treatment (data not shown).

Northern blot analysis indicated that c-myc mRNA is overexpressed in the cystic kidney and that overexpression is unaltered by c-myc ASO treatment. However, ASO treatment inhibited c-myc protein expression as evidenced by a decreased amount of detectable c-myc protein in kidneys from ASO-treated mice (an approximately 59% reduction by western blot analysis).

Northern blot analysis also indicated that EGF mRNA was highly expressed in normal kidney, but diminished in cystic kidney. Following c-myc ASO treatment EGF mRNA expression was increased nearly twelve fold in cystic kidney. mRNA for SGP-2, a marker typically expressed in immature collecting duct tissue, was overexpressed in cystic versus normal kidney, but was decreased approximately 40% after c-myc ASO treatment. Increased EGF mRNA and decreased SGP-2 mRNA expression indicate that c-myc ASO treatment led to an increased maturation of both the distal tubule and collecting duct, respectively. mRNA for Histone H4, a marker associated with increased cell proliferation, was overexpressed in cystic compared to normal kidney, however, c-myc ASO treatment did not significantly reduce the Histone H4 message level in cystic kidney. However, ASO treatment was associated with a 30% decrease in PCNA, a marker of cell proliferation (data not shown).

Further analysis indicated more c-myc protein in cystic compared to normal kidneys. Immunohistochemistry indicted that the c-myc was localized to the nuclei of epithelial cells lining cystic and noncystic tubules. After c-myc ASO treatment, the lower c-myc protein levels appeared to be due largely to a reduction c-myc in the noncystic tubules.

Analysis of renal c-myc ASO in kidney lysates from 20 day old c-myc ASO treated C57BL/6J-cpk mice indicated a concentration of 0.47 µM, while c-myc ASO was not detected in kidney lysate from 20 day old control C57BL/6J-cpk mice.

The efficacy of treatment with c-myc ASO was also evident in mice treated with higher (14.3 nM; 100 µg) and lower (1.4 nM; 10 µg) dosages of ASO. Relative kidney weight as well as SUN levels were reduced to a similar extent to that observed after treatment with 413 nM (30 µg) of c-myc ASO. Total body weight and hematocrit levels were also unaffected by these dosages of c-myc ASO.

These results suggest that c-myc antisense treatment can diminish the symptoms of PKD associated with c-myc over-expression in the kidney.

TABLE 2

Sequences Provided In Support Of The Application.

| Description | SEQ ID NO |
|---|---|
| antisense to c-myc AVI 4126 (1-22-126)<br>5'-ACG TTG AGG GGC ATC GTC GC-3' | 1 |
| c-myc antisense scramble control AVI 4144 (1-22-144)<br>5'-ACT GTG AGG GCG ATC GCT GC-3' | 2 |

Although the invention has been described with respect to compositions and methods, it will be appreciated that various changes and modifications may be made, within the scope of the claim, without departing the invention.

All publications, patents and patent applications are herein expressly incorporated by reference in their entirety to the same extent as if each individual publication, patent or patent application was specifically and individually indicated to be incorporated by reference in its entirety.

3. The method of claim 2, where said linkages include the phophorodiamidate linkage of structure II, where X=NH$_2$, Y=O, and Z=O, and Pi and P$_j$ are purine or pyrimidine base-pairing moieties effective to bind, by base-specific hydrogen bonding, to a base in a polynucleotide.

Structure II

What is claimed is:

1. A method of treating polycystic kidney disease (PKD) in a human or murine subject, comprising:
   administering to the subject a morpholino-based antisense oligomer having uncharged, phosphorous-containing intersubunit linkages, where the antisense oligomer contains the sequence identified as SEQ ID NO:1.

2. The method of claim 1, where the intersubunit linkages of said morpholino-based antisense oligomer are uncharged, phosphorous-containing linkages one to three atoms long, joining the morpholino nitrogen of one subunit to the 5' exocyclic carbon of an adjacent subunit.

4. The method according to claim 1, where said administering takes place by any one of an oral route, a subcutaneous route, an intranasal route, a transdermal route or an intravenous route.

5. The method according to claim 4, where said administering takes place by an oral route.

6. The method of claim 1, where said subject is a human subject.

7. The method according to claim 1, where the antisense oligomer is administered in a manner effective to reduce or eliminate a detectable symptom of PKD in the subject.

* * * * *